(12) United States Patent
Sinur et al.

(10) Patent No.: US 9,292,746 B2
(45) Date of Patent: Mar. 22, 2016

(54) AUTOMATED EMISSIONS CAPTURE DETERMINATION

(71) Applicant: Broan-NuTone LLC, Hartford, WI (US)

(72) Inventors: Richard R. Sinur, West Bend, WI (US); Eric Williams, Grafton, WI (US); Joseph Brandon Adamo, Provo, UT (US)

(73) Assignee: Broan-NuTone LLC, Hartford, WI (US)

( * ) Notice: Subject to any disclaimer, the term of this patent is extended or adjusted under 35 U.S.C. 154(b) by 115 days.

(21) Appl. No.: 14/282,649

(22) Filed: May 20, 2014

(65) Prior Publication Data

US 2015/0339528 A1 Nov. 26, 2015

(51) Int. Cl.
*G06K 9/00* (2006.01)

(52) U.S. Cl.
CPC ................... *G06K 9/00624* (2013.01)

(58) Field of Classification Search
USPC ........................................... 382/103
See application file for complete search history.

(56) References Cited

U.S. PATENT DOCUMENTS

| | | | |
|---|---|---|---|
| 7,147,168 B1 * | 12/2006 | Bagwell ............... | B08B 15/00 165/237 |
| 2009/0159798 A1 | 6/2009 | Weida et al. | |
| 2011/0038507 A1 * | 2/2011 | Hager ................... | G01N 21/33 382/100 |
| 2011/0253693 A1 | 10/2011 | Lyons et al. | |

FOREIGN PATENT DOCUMENTS

KR 10-2012-0050073 A 5/2012

OTHER PUBLICATIONS

"International Application Serial No. PCT/US2015/031135, International Search Report mailed Sep. 7, 2015", 3 pgs.
"International Application Serial No. PCT/US2015/031135, Written Opinion mailed Sep. 7, 2015", 11 pgs.
"International Standard 61591—Household range hoods—Methods for measuring performance", © IEC 1997, (1997), 34 pgs.
"Standard Test Method for Capture and Containment Performance of Commerical Kitchen Exhaust Ventilation Systems", F1704-05, Copyright ASTM International, (2007), 10 pgs.

* cited by examiner

*Primary Examiner* — Gregory F Cunningham
(74) *Attorney, Agent, or Firm* — Schwegman Lundberg & Woessner, P.A.

(57) ABSTRACT

A method of determining emissions captured can include receiving information indicative of transmission of light through a region nearby an air handling apparatus. The information can include information indicative of a first condition wherein emissions to be captured by the air handling apparatus are suppressed and information indicative of a second condition wherein the emissions to be captured by the air handling apparatus are present. A processor circuit can be used to determine a difference between the information about the transmission of light during the first condition and information about the transmission of light during the second condition. The processor circuit can be used to determine a portion of the emissions captured by the air handling apparatus using information about the determined difference.

30 Claims, 9 Drawing Sheets

AUTOMATED EMISSIONS CAPTURE DETERMINATION

BACKGROUND

Range hoods, exhaust fans, or other air handling apparatus have long been used in home, commercial, and industrial environments to assist in treating (e.g., filtering) or removing pollutants or other emissions. Various attempts have been made to compare the relative effectiveness of one air handling system to another, particularly in relation to air handling apparatus for use in exhausting or filtering cooking emissions. In one approach, an amount of emissions captured by a range hood can be assessed indirectly. For example, this can be accomplished by mechanically measuring an exhaust flow rate through an aperture such as an exhaust duct. However, while such an approach can provide a numerical result (e.g., cubic feet per minute (CFM)) such indirect assessment has drawbacks because it only considers one aspect of range hood efficiency and may deliver biased results. For example, such an approach does not provide information as to the spatial coverage or "reach" of the air handling apparatus being evaluated.

In another approach, ASTM standard F1704-05, "Standard Test Method For Capture and Containment Performance of Commercial Kitchen Exhaust Ventilation Systems" provides a method of measuring an exhaust flow rate through an air system using flow visualization to determine the threshold of capture and containment (C&C) of a hood/appliance combination under cooking and idle conditions.

OVERVIEW

As mentioned above, existing approaches generally fail to quantify a portion of emissions captured by an air handling apparatus. The present inventors have recognized, among other things, that determination of emissions captured can be partially or entirely automated, such as using image processing techniques. Use of such image processing techniques performed on images obtained digitally to provide a repeatable assessment of an effectiveness of a range hood or other air circulating apparatus, such as including providing a numerical determination of such performance.

In an example a shadow graph image can be obtained such as using a digital camera configured to image a test configuration that can include one or more of a stove, a heating element, an emitting vessel such as a pot or other vessel, and an air handling apparatus such as a range hood. An associated capture region can be defined nearby an intake portion of the air handling apparatus, such as defined by a region below the range hood or adjacent to a down-flow range vent system. The heating element can be used to heat the cooking vessel to generate emissions, some or all of which can be captured by the air handling apparatus.

The shadow graph imaging technique can be used to reveal portions of the emissions that would otherwise be invisible or difficult to observe. In an example, shadow graph imaging can be performed during an "idle" state, such as where the emissions are suppressed. Shadow graph imaging can also be performed over a specified duration such as in an "active" state, such as where emissions are present. A difference between imaging information obtained using a shadow graph image in an active state and a shadow graph image in an idle state can be used to identify regions where emissions are present. Then, for example, a portion of the emissions within a defined capture region can be compared to a portion of the emissions existing elsewhere and the determined difference can be used to estimate a "capture efficiency" or one or more other parameters. One or more test parameters can be obtained from a user such as using a graphical user interface, and one or more results of such capture efficiency determination can be presented to a user using such a graphical user interface.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals can describe similar components in different views. Like numerals having different letter suffixes can represent different instances of similar components. The drawings illustrate generally, by way of example, but not by way of limitation, various embodiments discussed in the present document.

DETAILED DESCRIPTION

Figure 1:
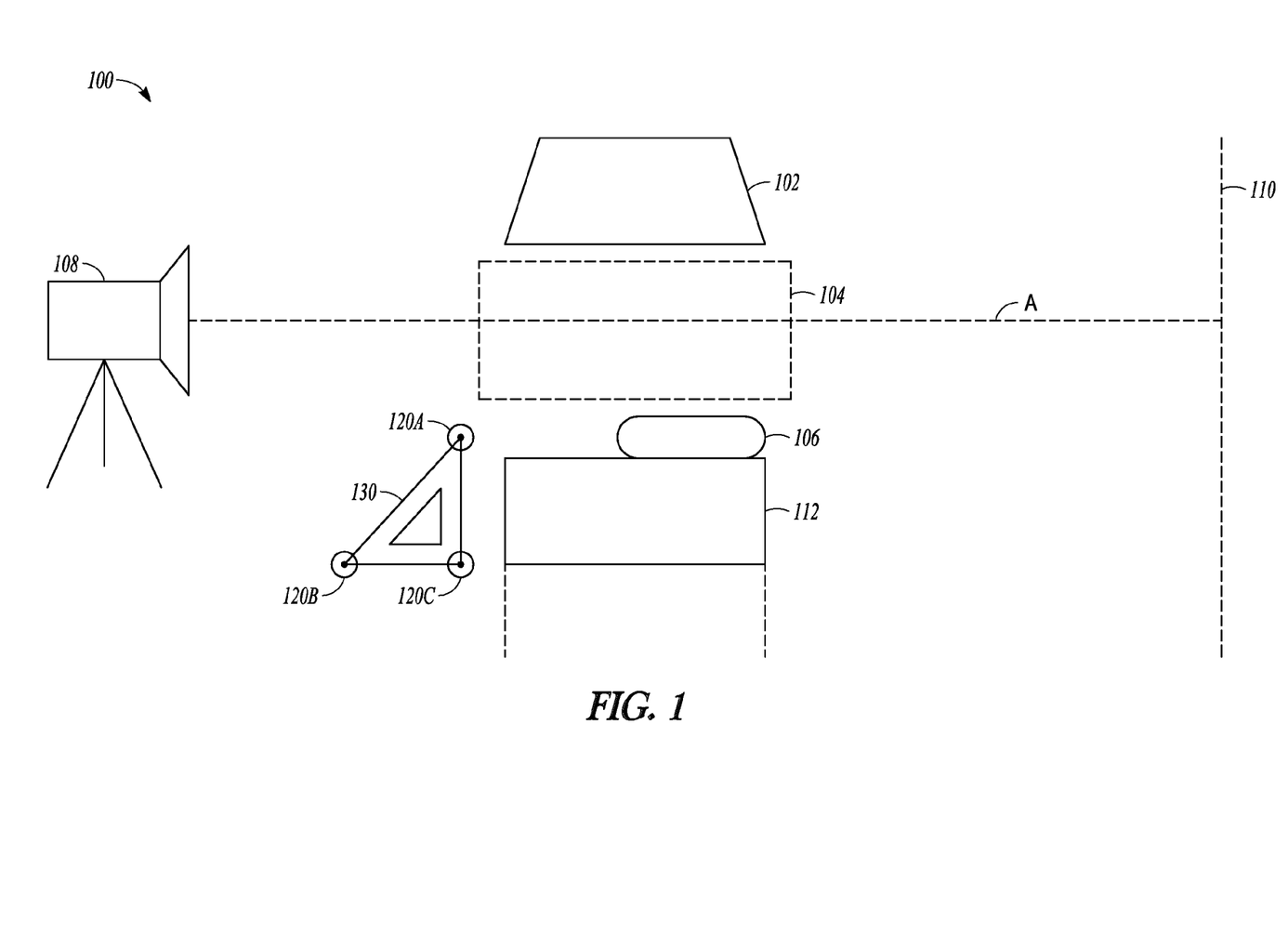
FIG. 1 illustrates generally an example of a system for determining emissions captured by an air handling apparatus, such as including a vent hood, a capture region, and a camera.

FIG. 1 illustrates generally an example of a system 100, such as can be used for determining emissions captured by an air handling apparatus. The system 100 can include one or more of an air handling apparatus such as a vent hood 102. A capture region 104 can be defined, such as nearby an air intake of the air handling apparatus. Such a capture region 104 can be used in determining a capture efficiency of the air handling apparatus. For example, an imaging apparatus, such as a camera 108, can be used to obtain information indicative of transmission of light through the capture region 104 or other regions. In an example, a cooking surface can be provided or emulated, such as can include a heating vessel 106, such as a pot or a pan. The heating vessel 106 can include water or can include a source of particulate emissions such as a smoke source, or the like, and can sit on a on a support structure 112. The support structure 112 can be a stove, or can include multiple features to provide a configuration similar to a stove, for example, such as a hotplate supported by a frame structure.

As shown in the example of FIG. 1, the capture region 104 can be defined above the heating vessel 106, such as in a region where an emissions capture efficiency of the vent hood 102 is to be determined. In an example, the camera 108 can obtain information indicative of transmission of light through the capture region 104 along an axis, "A." The information can include an image projected on a surface 110 (e.g., a screen onto which a "shadow" of the test setup is cast). The surface 110 can be illuminated by a light source located within or nearby the camera 108. In this manner, a beam of light projected from a location at or nearby the camera 108 can propagate through the capture region 104, and a resulting image projected by the light on the surface 110 can provide an indication of a location of emissions, such as due to a spatially or temporally varying index of refraction or absorption through the capture region 104. Such an imaging technique can be referred to generically as a "shadow imaging" or "shadow graph" technique.

In an example, the system 100 can include a dimensional reference 130, such as a ruler, square, or other structure having known or easily measureable dimensions. The dimensional reference 130, can be used such as for manually or automatically determining or estimating dimensions of other features of the system 100 when the dimensional reference 130 is imaged. For example, either manually (e.g., via a user interface as discussed in other examples herein) or automatically, the system 100 can use features of the dimensional reference 130, such as one or more of a first dimensional reference location 120A, second dimensional reference location 120B, or third dimensional reference location 120C, such as to establish a relationship between physical dimensions and obtained imaging information (e.g., to calibrate lengths in the obtained imaging information).

As discussed in other examples herein, a location of the camera 108 can affect a repeatability or accuracy of a determined capture efficiency, such as due to one or more of perspective effects or obstructions present in the imaging field. Accordingly, the camera 108 or apparatus being imaged can be repositioned for various imaging operations, or multiple cameras can be used. For example, one or more of the camera 108 or the surface 110 can be arranged such that the axis A traverses a central portion or centroid of the capture region 104, or some other specified portion of the capture region 104, or using one or more other alignments. The camera 108 can be aligned such that the axis A is orthogonal to the surface 110. In FIG. 1, emissions are not shown in the capture region 104 or elsewhere, such as corresponding to an idle state, such as where emissions are suppressed.

In an illustrative example, the system 100 can include a residential system, such as a residential kitchen setup. The vent hood 102 can include a residential vent hood, such as a home kitchen vent hood, a home kitchen range hood, a home kitchen downdraft ventilator, an under-cabinet range hood, a hidden range hood, a built-in home range hood, a wall mounted home range hood, a home chimney, a home island range hood, or the like. FIG. 1 can include a test configuration such as a representation of a residential kitchen. In an example, the heating vessel 106 can include a household pot or pan.

Figure 2A:
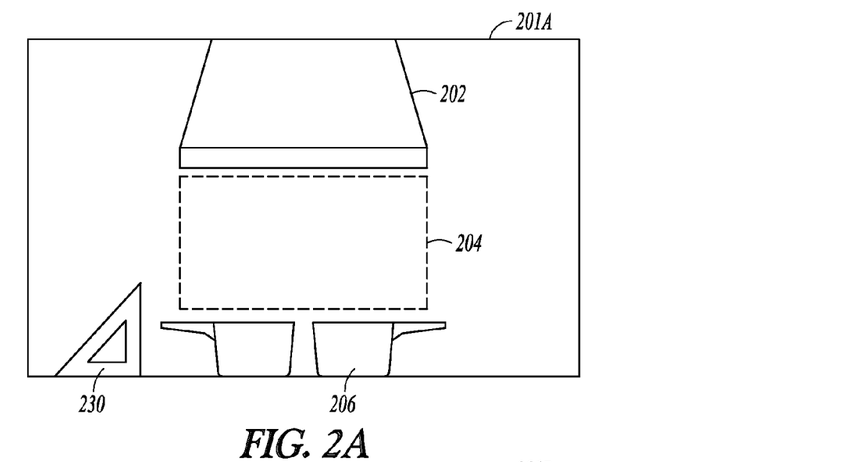
FIG. 2A illustrates generally an example diagramming a representation of a captured image showing a front-view emissions capture testing configuration, such as in an idle state where the emissions are suppressed.

FIG. 2A illustrates generally an example diagramming a representation of an image 201A (e.g., representing a digital image captured by digital imaging apparatus or provided by a user) showing a front-view emissions capture testing configuration, such as in an idle state where the emissions are suppressed. The image 201A can depict one or more the elements described above such as a vent hood 202, a capture region 204 (e.g., as defined by a user or as can be automatically determined), a heating vessel 206, or a dimensional reference 230. The vent hood 202 can include a mounting configuration similar to the intended use of the vent hood 202 when installed in a dwelling, such as a mounting to a wall or ceiling, or including a mounting configuration emulating such use.

In the example of FIG. 2A, corresponding to an idle state where emissions are suppressed, emissions are not shown in the capture region 204. Such a configuration can be used to provide a "baseline" for comparison with other states, such as the "active" state shown in FIG. 2B, for example. For example, the image 201A can include an image projected on a surface 110 illuminated by a light source located within or nearby the camera 108 from FIG. 1, generally known as a "shadow image" or a "shadow graph image." The capture region 204 can include a specified region, such as a user-specified region. The image 201A can also include determining the capture region 204, such as by using information about the vent hood 202 or the heating vessel 206.

Figure 2B:
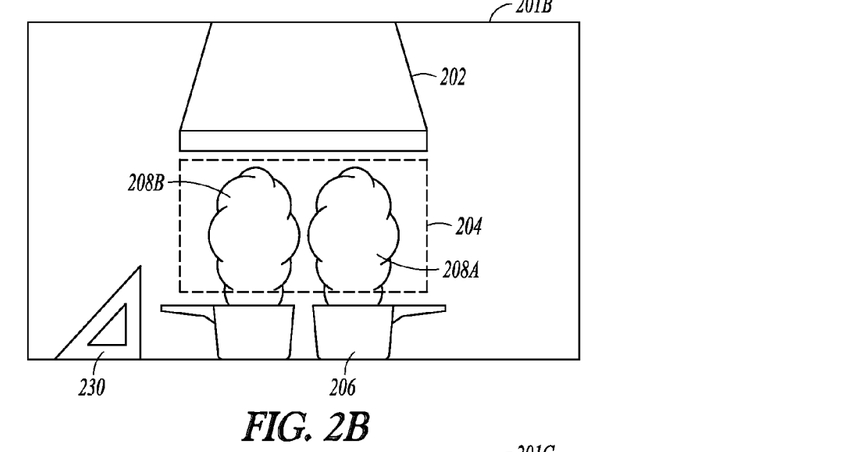
FIG. 2B illustrates generally an example diagramming a representation of a captured image showing a front-view emissions capture testing configuration, such as in an active state where the emissions are present.

FIG. 2B illustrates generally an example diagramming a representation of a captured image showing a front-view emissions capture testing configuration, such as in an active state where the emissions are present. In FIG. 2B, emissions are shown within the boundary of the capture region 204 and elsewhere. Such emissions are shown by emissions "plumes" 208A or 208B, and in actual obtained images such "plumes" generally appear as regions where intensity varies spatially and temporally. The emission plumes 208A or 208B can include one or more of particulate matter, such as cooking effluent, water vapor, smoke, fumes, or the like.

Figure 2C:
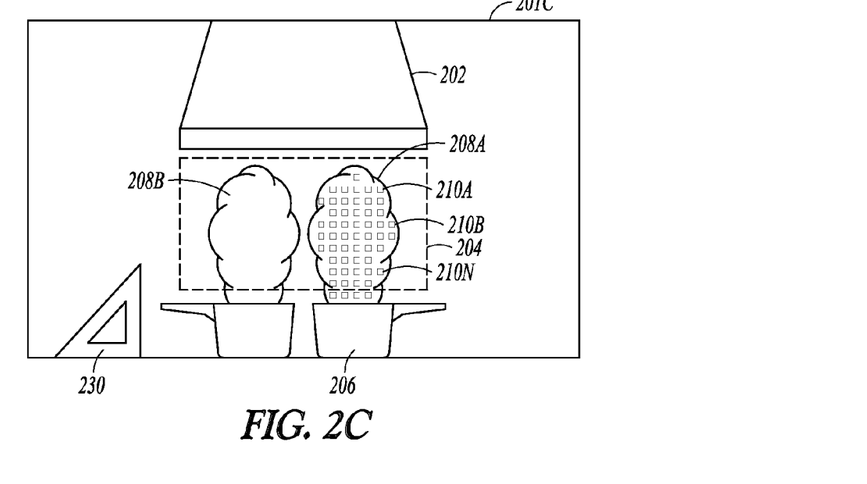
FIG. 2C illustrates generally an example diagramming a representation of a generated image showing a front-view emissions capture testing configuration, such as in an active state where the emissions are present including an illustrative example of locations highlighted as a portion of an emissions plume.

A difference between information about the transmission of light during the first condition shown in FIG. 2A and information about the transmission of light during the second condition shown in FIG. 2B can be used to identify a locus of the emissions plumes 208A or 208B, as shown in FIG. 2C. In an example, a portion of the emissions captured by the air handling apparatus can be determined using information about where the emissions plumes 208A or 208B are located with respect to the capture region 204.

FIG. 2C illustrates generally an example diagramming a representation of a generated image 201C showing a front-view emissions capture testing configuration, such as in an active state where the emissions are present and including an illustrative example of locations highlighted as a portion of an emissions plume. In FIG. 2B, emissions are shown in the capture region 204 and elsewhere. The locations of one or more portions of plumes 208A or 208B can be automatically determined on a location-by-location basis, such as on a pixel-by-pixel basis.

For example, individual pixels or groups of pixels can be classified as "members" of a set of pixels or locations defining the emissions plumes 208A or 208B automatically using information about bitmap representations of the images 201A or 201B. In an illustrative example, a pixel intensity value for a specified location 210A can be extracted from a baseline image, such as a baseline pixel intensity value for location 210A in an idle state (e.g., as in FIG. 2A), and a corresponding pixel intensity value can be extracted from an image for location 210A corresponding to an active state (e.g., as in FIG. 2B). A difference between the two extracted intensity values can be determined.

When the difference exceeds a specified threshold, the pixel location 210A can be classified as a member of the set of pixels or locations defining the emissions plume 208A or 208B. In other approaches, a pixel location 210A can be compared with an aggregated background pixel intensity value, such as an established baseline value, or a central tendency of background values such as an average background value, a normalized background value, or other central tendency, such as determined using the image 201A in an idle-state as a baseline. A similar determination can be made at other locations 210B through 210N. In this manner, the location of the emissions plumes 208A or 208B can be automatically determined. Such techniques can be used on aggregated groups of pixels, and such determinations can be made across a variety of regions. Such techniques can generally be referred to as emissions location detection or plume detection.

One or more parameters used in relation to the capture detection techniques described herein can be automatically determined or user-adjustable such as using a graphical user interface as described in other examples herein. In an example, to aid such parameter evaluation, locations or pixels identified as being "members" of a detected emissions plume 208A or 208B can be highlighted, such as shown diagrammatically in FIG. 2C or 8A. In this manner, a user can rapidly evaluate an effect of a given set of parameters by observing whether the highlighted (e.g., detected) portion of the plume corresponds to an actual location or area of the plume across an image or a range of images.

Figure 3:
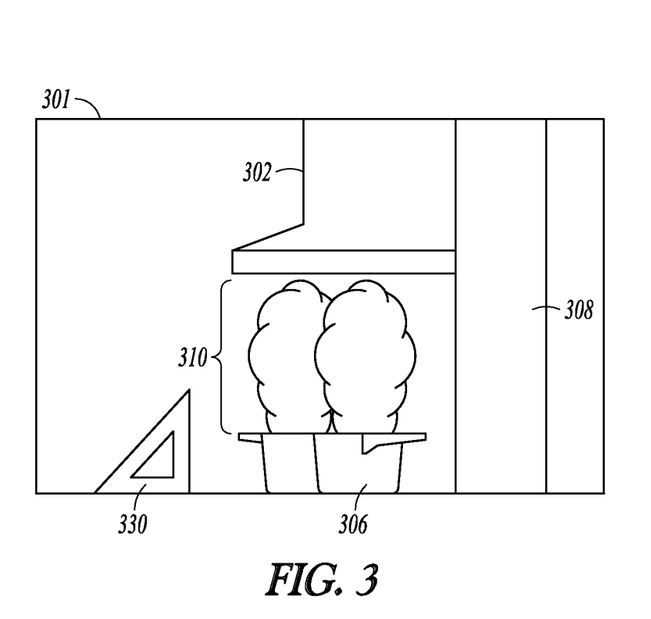
FIG. 3 illustrates generally an example diagramming a representation of a captured image showing a side-view emissions capture testing configuration, such as in an active state where the emissions are present, such as can include a back wall.

FIG. 3 illustrates generally an example diagramming a representation of an image 301. The image 301 can include information indicative of transmission of light through a region, similar to the examples of FIGS. 2A through 2C but including a different alignment of the imaging apparatus or screen for side-view imaging. In this manner, information about the location of emissions 310 can be aggregated or otherwise obtained to avoid possible error associated with using information obtained only from a single imaging axis.

The obtained image 301 can include one or more of the elements described above such as a vent hood 302, a heating vessel 306, or a dimensional reference 330. In an example, the obtained image 301 can include partition 308, such as a wall, a column of air, or any other apparatus or that partially or completely prevents emissions from bypassing the vent hood 302. In this manner, the test configuration can be established in a manner that emulates an actual vent hood 302 installation configuration, such as against a wall. In an example, the vent hood 302 can include being attached to the partition 308. For example, the vent hood 302 can be designed to work with the partition 308 to increase emissions captured.

Figure 4:
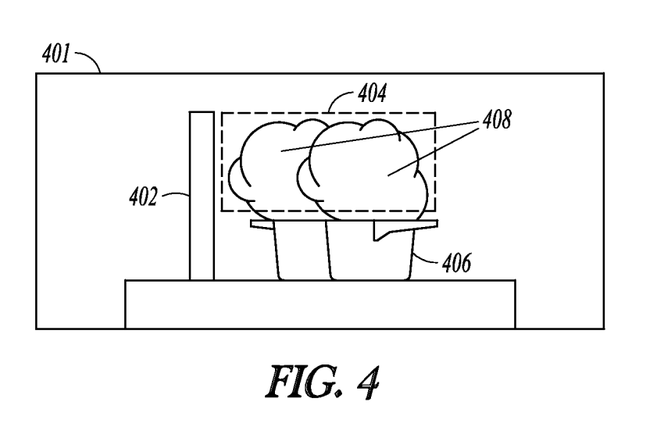
FIG. 4 illustrates generally an example diagramming a representation of a captured image showing a side-view emissions capture testing configuration, such as with a downdraft vent in an active state where the emissions are present.

The illustrations of the FIGS. 1, 2A through 2C, and FIG. 3 generally illustrate overhead air handling configurations, such as corresponding to a range or other ventilation hood mounted above a source of emissions. Other configurations can also be evaluated, such as down-flow configuration as shown in FIG. 4. FIG. 4 illustrates generally a diagrammatic representation of an image 401 that can be obtained, such as using a shadow imaging technique as in other examples. In FIG. 4, emissions are shown in the capture region 404, as described above. The obtained image 401 can include one or more of the elements described above such as a heating vessel 406, a support structure 412, or a dimensional reference 430. Emissions can be present, such as at 408A or 408B. In an example, obtained image 401 can include one or more of an air handling apparatus such as a down-draft ventilator 402. The obtained image 401 can include a capture region 404 associated with the down-draft ventilator 402 that is similar to the capture region 204 associated with the vent hood 202 of FIG. 2A.

Figure 5:
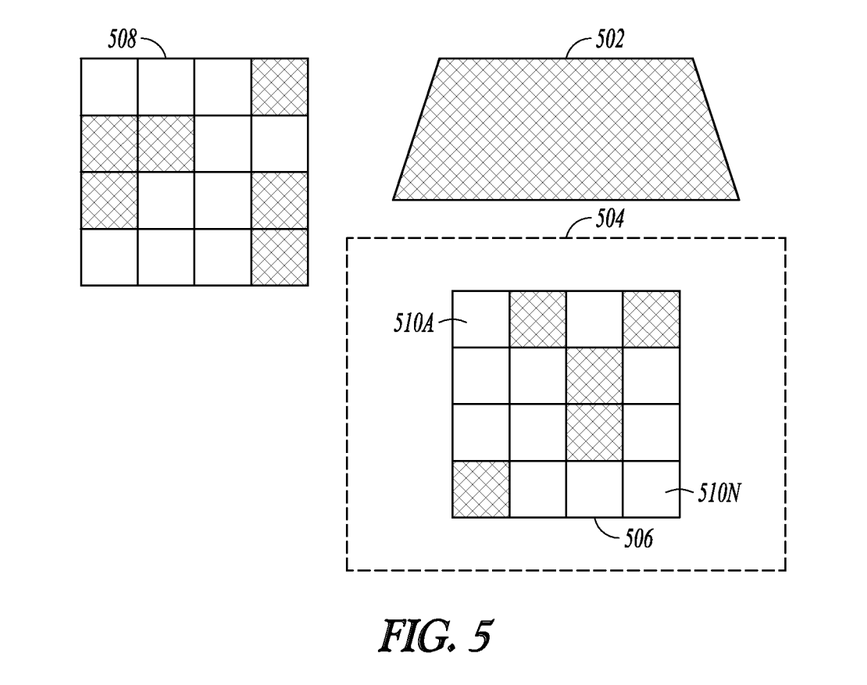
FIG. 5 illustrates generally illustrative examples of regions that can be processed, such as to provide bitmap representation for use in an emissions capture determination.

FIG. 5 illustrates generally illustrative examples of regions that can be processed such as to determine a presence or absence of an emissions plume, or to identify locations as members of a set of locations comprising an emissions plume. In an example, FIG. 5 can include one or more elements described above such as a vent hood 502 and a capture region 504. A first processed region can include a first bitmap representation 506 inside the capture region 504 comprising a representation of portions of an emissions plume. For example, membership in a set of emissions locations can be determined on a location-by-location basis, such as starting at a location 510A through a location 510N. A second processed region can include a second bitmap representation 508 outside the capture region 504 comprising a representation of emissions plume such as including portions determined on a location-by-location basis.

In an example, FIG. 5 can include determining whether a location, such as a specified location 510N, should be included in a set of locations defining an emissions plume. For example, for the specified location 510N, a baseline intensity value can be determined corresponding to a first condition, such as an "idle" state as described above in relation to image 201A. The determination can include identifying a second intensity value for the specified location 510N using a bitmap representation obtained during a second condition, such as corresponding to an "active" state described above in relation to the image 201B. A difference between the second intensity value for the specified location 510N and the baseline intensity value for the specified location 510N can be determined. If the determined difference meets one or more specified criteria, such as having an absolute or relative difference greater than a specified threshold, the location 510N can be classified as belonging to a set of locations defining an emissions plume.

A similar location-by-location (e.g., pixel-by-pixel) determination can be made in relation to the second bitmap representation 508 outside the capture region 504. The second bitmap representation 508 can include a subset of image locations from a digital image, such as corresponding to some or all locations outside the capture region 504, and the first bitmap representation 506 can include locations within the capture region 504.

In an example, determining a portion of emissions captured by an air handling apparatus can include determining a first locus of locations comprising an emissions plume, inside the capture region 504 such as corresponding to the first bitmap representation 506. Determining a portion of emissions captured by an air handling apparatus can also include determining a second locus of locations, such that some or all locations are outside the capture region 504, such as corresponding to the second bitmap representation 508.

A portion of emissions captured by an air handling apparatus can include, for example, a ratio (e.g., expressed as a decimal proportion or percent) or other relative indication of the number of locations in the first locus of locations and the number of locations in the second locus of locations or a relative indication of the area comprising the first locus (e.g., within the capture region 504) versus the second locus. For example, the number of locations in a locus of locations can include a number of pixels identified as members of an emissions plume, such that the portion of emissions captured by an air handling apparatus can include a ratio of the number of pixels in the first locus of locations and the number of pixels in the second locus of locations. In the diagrammatic illustration of FIG. 5, the shaded regions can indicate locations determined to be a portion of the emissions plume, such as can be highlighted using a selected color or brightness value when presented to a user.

Vibration of the test apparatus, or other sources of error can confound the determination of whether a given area of an image should be considered a portion of an emissions plume. The present inventors have also recognized that a "dead" zone or "erosion" zone can be established, such as in relation to a boundary of one or more fixed elements in the image. In such a zone, emissions can be ignored or determination of membership in an emissions plume can be suppressed.

Figure 6:
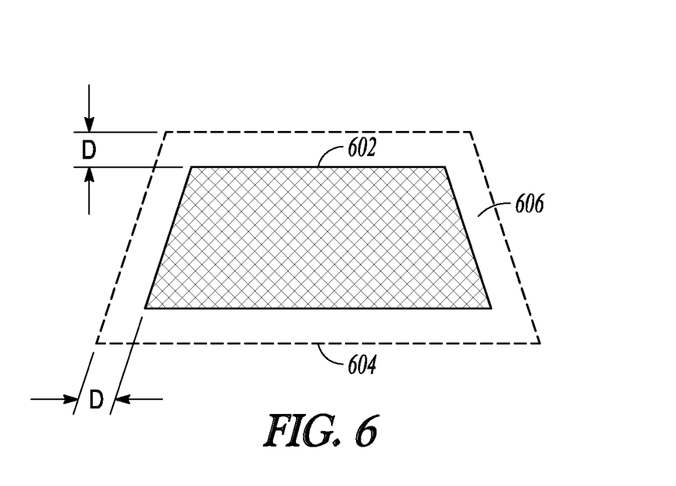
FIG. 6 illustrates generally an example of a region including a locus of locations where emissions can be ignored, such as surrounding an imaging feature (e.g., a ventilation hood).

For example, FIG. 6 illustrates generally an illustrative example of a region including a locus of locations where emissions can be ignored, such as surrounding an imaging feature (e.g. a vent hood). FIG. 6 can comprise a boundary region 606 surrounding a vent hood 602. In an example, FIG. 6 can include a boundary region 606 surrounding the vent hood 602, such that a distance D separates the vent hood 602 from the edge of a boundary region 604. The vent hood 602 can itself establish a dark region having well-established boundaries when shadow-imaged. Such a dark shadow can be automatically identified, such as comprising a locus of locations having an intensity value below a specified absolute threshold (e.g., casting a dark shadow). The boundary region 606 can include a locus of locations within a specified distance D of the locations having an intensity value below the specified absolute threshold. For example, determining a portion of emissions captured by an air handling apparatus can include ignoring the intensity values for the locus of locations within the boundary region 606.

Other features can be ignored as well, such as values for the locus of locations within a boundary region of one or more elements, such as the heating vessel 106, the support structure 112, the vent hood 102, the dimensional reference 130, the down-draft ventilator 402, and the like. In this manner, slight variations in imaging apparatus positioning (e.g., camera angle), or vibration of the test setup during obtaining multiple imaging frames will not create significant errors. In an example, the erosion zone boundaries can be user-selectable or can include using information obtained from as user, such as to assist in establishing a stable and repeatable test setup.

Figure 7:
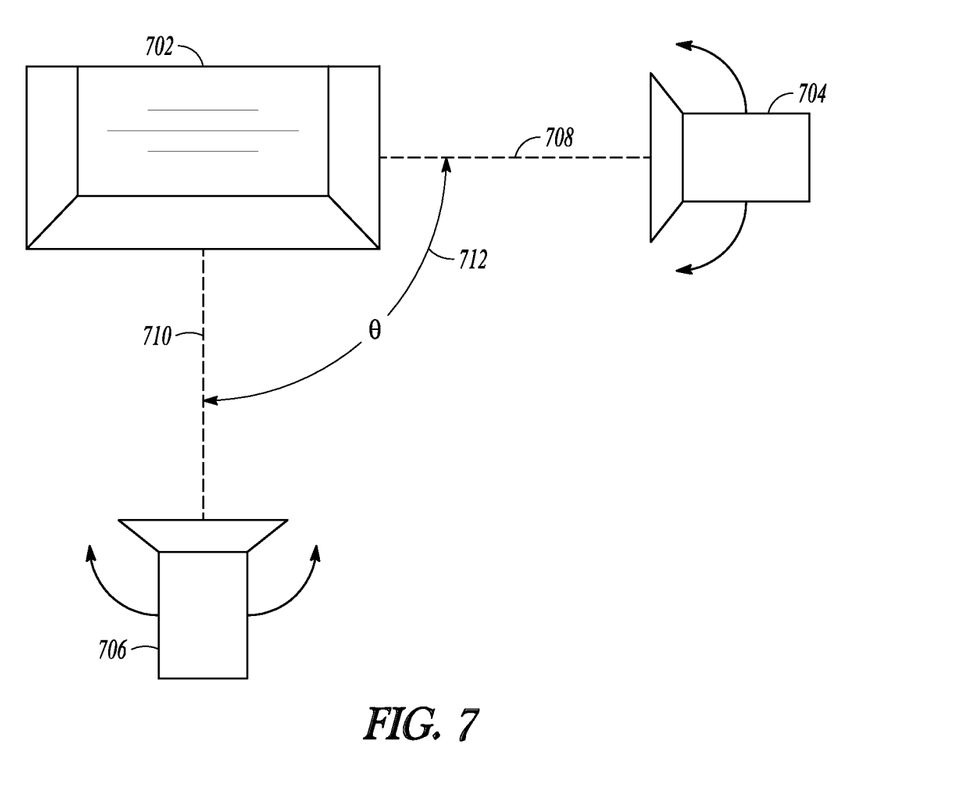
FIG. 7 illustrates generally an overhead view of an example of a system for determining emissions captured by a hood, including a hood, multiple cameras for capturing information, and information about the relationships among the cameras and the hood.

FIG. 7 illustrates generally an overhead view of an example of a system, such as can be used for determining emissions captured by an air handling apparatus. The system can include one or more of an air handling apparatus such as a vent hood 702. The example of FIG. 7 illustrates generally that imaging can be performed from multiple vantage points, such as for use in aggregating one or more emission capture efficiency determinations to avoid errors due to perspective view, obstructions, or other more general limitations of imaging a three dimensional capture volume using two-dimensional snapshots and processing techniques.

An imaging apparatus, such as a side camera 704 or a front camera 706, can be used to obtain information indicative of transmission of light through the capture region or other regions. In an example, information indicative of variation in transmission of light through a region nearby the air handling apparatus can include digital imaging. The information indicative of the variation in transmission of light through the region nearby the air handling apparatus can include digital imaging corresponding to at least two view angles, such as from the side camera 704 and the front camera 706. In an example, the at least two viewing angles can include a pair of viewing angles that are substantially orthogonal to each other, such as when the relative camera angle, "Θ" 712 is approximately a right angle. The pair of viewing angles can be orthogonal to each other, such as when the relative camera angle "Θ" 712 is a right angle.

In an example, the front camera 706 can include a front imaging axis 710, such that the front imaging axis 710 is orthogonal or substantially orthogonal to a front edge of the vent hood 702. The side camera 704 can include a side imaging axis 708, such that the side imaging axis 708 is orthogonal or substantially orthogonal to a side edge of the vent hood 702. The front camera 706 or the side camera 704 can be separate cameras, or the test setup can be configured so that a camera location is rotated relative to the vent hood 702, or to any other element of the system. For example, the vent hood 702 can be mounted on a platform or otherwise configured to rotate relative to the front camera 706, or vice versa.

In an example, receiving information indicative of transmission of light through a region nearby an air handling apparatus can include receiving an image or a series of images of a surface illuminated by the light after propagating through a region nearby the air handling apparatus. For example, the image or series of images can include an image or series of images taken by the front camera 706 or an image or series of images taken by the side camera 704, as described in examples above and below.

Figure 8A:
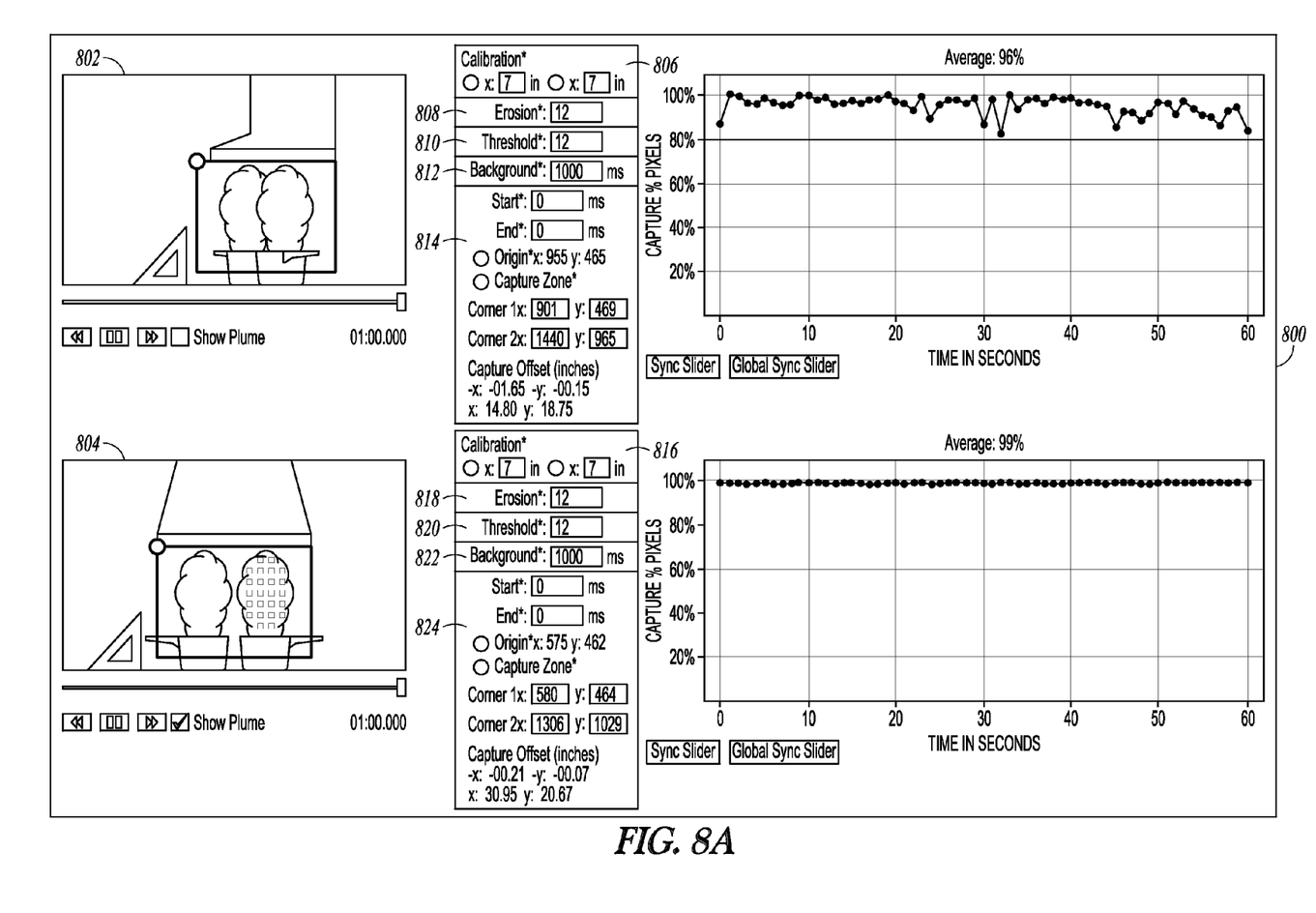
FIGS. 8A and 8B illustrate generally illustrative examples of a user interface that can be used to present information related to determination of capture of emissions by a hood, and inputs that can be used to control such determination.
Figure 8B:
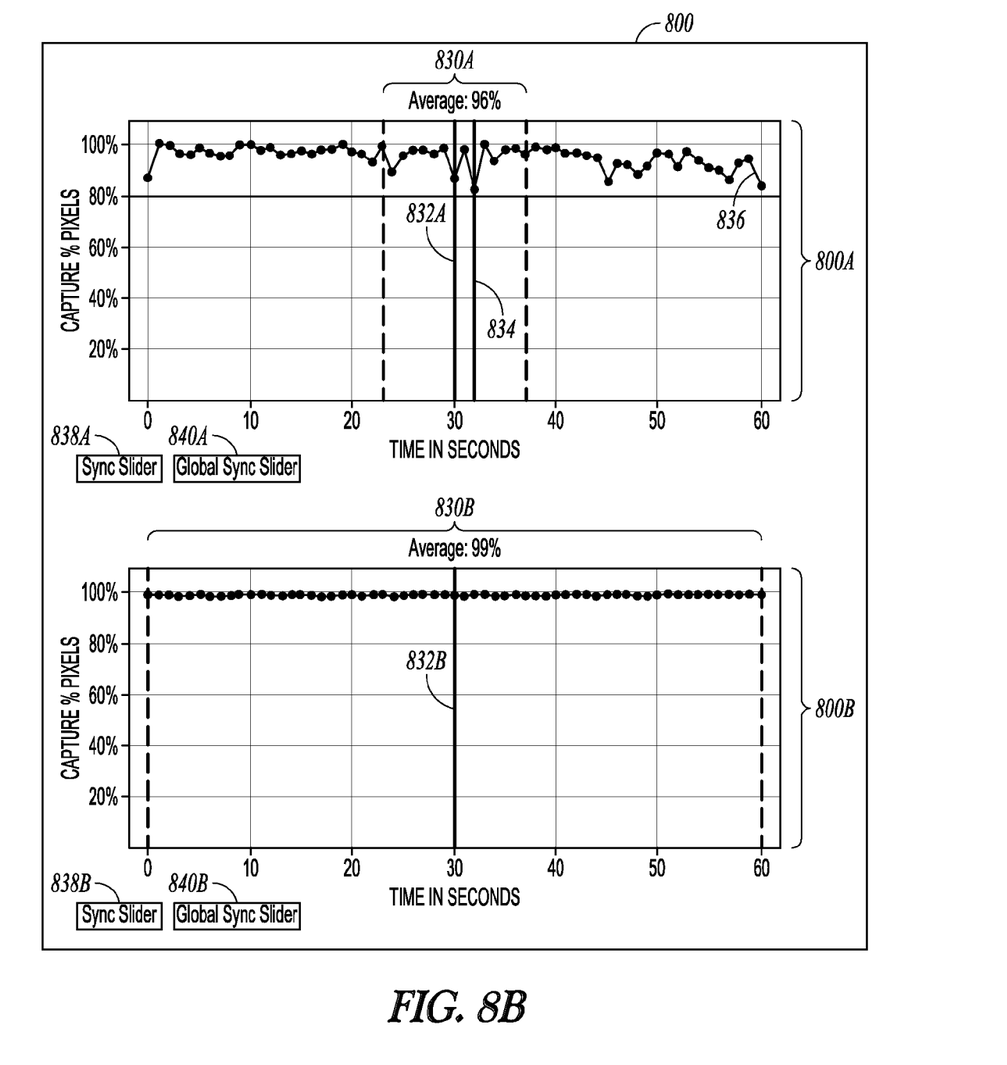

FIG. 8A illustrates generally an illustrative example of a user interface 800. Such a user interface can be presented to a user, such as using a processor circuit coupled to a memory circuit, the memory circuit including instructions that, when performed by the processor circuit, cause the processor circuit to one or more of present information to a user or receive information from a user, such as using a graphical representation of the information as shown in FIG. 8A or 8B. In an example, the user interface 800 can present an obtained side image 802 or an obtained front image 804. In an example, the obtained front image 804 can include a graphical representation of a specified locus of locations, such as including identifying an effluent plume. For example, the obtained front image 804 can also include a highlighted region of the effluent plume on the graphical representation, such as by using one or more of a specified intensity or color (e.g., providing a false color representation of the plume region to aid a user in identifying the plume region, such as during tuning by the user of one or more test parameters). The obtained front image 804 can include a user selected option to toggle the visibility of the graphical representation or the highlighting, (e.g., a "Show Plume" checkbox).

The user interface 800 can also include a side dimensional reference interface 806 or a front dimensional reference interface 816. In an example, the side dimensional reference interface 806 can comprise a user specified length corresponding to a determined distance between two points, such as between a first dimensional reference location 120A and a third dimensional reference location 120C. The side dimensional reference interface 806 can include multiple user specified lengths, such as to determine a horizontal reference distance and a vertical reference distance.

In an example, the user interface 800 can include a user-adjustable erosion zone 808 for the obtained side image 802 or a user-adjusted erosion zone 818 for the obtained front image 804. The user-adjustable erosion zone 808 can comprise an erosion zone corresponding to the distance D shown illustratively in FIG. 6, such as to establish a dead zone around the vent hood 602 or other static features. The boundary value can be a user specified physical distance, pixel distance, distance between two specified locations (e.g., pixels or points) in the image, such as locations identified by a user, or the like.

The user interface 800 can include one or more of a side threshold indicator 810 or a front threshold indicator 820. For example, if the images corresponding to the obtained front image 804 or the obtained side image 802 were obtaining using different lighting conditions, brightness, or contrast adjustments, then a corresponding threshold used for plume determination might be tailored to a specific view or camera orientation.

In an example, the side threshold indicator 810 can one or more of receive or display a threshold that can be used for classifying a location as a member of an effluent plume, as described in examples above. For example, when a determined difference between first and second conditions exceeds the specified threshold as indicated by a comparison, a location such as a pixel can be determined to be a member of an effluent plume. For example, the side threshold indicator 810 can comprise a user specified threshold, such as by a user indicating a number, by a user selecting a location or pixel in an image, or the like. The side threshold indicator can also be used to indicate an automatically-determined threshold.

The side threshold indicator 810 can include an absolute threshold. For example, the side threshold indicator 810 can comprise a user specified absolute threshold, such as by a user indicating a number, by a user selecting a location or pixel in an image, or the like. The side threshold indicator 810 can also be used to determine the absolute threshold, also using information from an image, information from a camera, or the like. The absolute threshold can be used to ignore a location (e.g., a pixel or a point) associated with a specified intensity value when the absolute threshold exceeds the intensity value.

In an example, the user interface 800 can include a control for selecting an image or range of images for use as a "baseline." For example, a side view baseline control 812 or a front view baseline control 822. For example, the side base frame interface can include a specified value corresponding to a particular image, frame, set of information, or the like. The particular image can include an image similar to 201A, such as where emissions are not present in the capture region 204, or elsewhere, such as corresponding to an idle state, such as where emissions are suppressed.

The user interface 800 can include a side-view capture region control 814 or a front-view capture region 824. In an example, the side-view capture region control 814 can be used to one or more of present a capture region or receive one or more indicia of a location of a capture region from a user. The capture region location can be specified by identification of an area, such as using pixel coordinates, or using calibrated units of length, such as in relation to a dimensional reference (e.g., a ruler, scale, or the like, placed within the field of vision). In an example, the side-view capture region control 814 can include a specified range corresponding to particular images, frames, sets of information, or the like.

In the illustrative examples of FIGS. 8A and 8B, the imaging information can include video imaging information. Accordingly, a capture determination can be performed over a range of video frames, such as to present a running profile of capture efficiency (e.g., as shown at right in FIG. 8A labeled "CAPTURE % PIXELS" versus "TIME IN SECONDS.").

FIG. 8B illustrates generally such a running capture determination, including various user-selectable indicia. For example, the user interface 800 can include a specified duration over which capture determination is performed. Such a duration can be specified in terms of start and stop times (e.g., numerically, as in FIG. 8A), or via receiving a user selection of a start and stop time by selection of one or more movable or positionable bars (e.g., one or more slider bars).

In an example, the user interface 800 can include a plot 836. The plot 836 can include information indicative of a portion of emission capture. For example, the plot 836 can comprise information about an image or a series of images related to the percentage of emissions captured by a vent hood in the image or series of images.

For example, a calculation range 830A or 830B can include a range corresponding to particular sequence of images, video frames, or the like. The user interface 800 can include calculating a central tendency across the calculation range 830A, such as a mean, median, or the like. In an example, the user interface 800 can include a side view graph 800A, a front view graph 800B, a side local frame value 832A or a front local frame value 832B. The side local frame value 832A can include displaying an obtained side image 802 corresponding to a particular image, frame, set of information, or the like. In the example of FIG. 8B, where two views are used (e.g., a front view and a side view), one or more user-selectable indicia can be slaved between the capture determination displays. For example, selection by a user of a side local frame value 832A in the side view graph 800A display can automatically generate a corresponding front local frame value 832B location in the front view graph 800B display. Additionally, still frames from a video file for each view corresponding to the selected time indicium can be automatically displayed, such as shown diagrammatically in FIG. 8A. Such an indicium can be referred to generically as a global frame value 834. In an example, the global frame value 834 can include displaying an obtained side image 802 and an obtained front image 804 corresponding to particular images, frames, sets of information, or the like.

The user interface 800 can include a side local frame value selection button 838A corresponding to the side local frame value 832A, a front local frame value selection button 838B corresponding to the front local frame value 832B, a side global frame value selection button 840A corresponding to the global frame value 834, or a front global frame value selection button 840B corresponding to the global frame value 834. In an example, the side local frame value selection button 838A can include causing the obtained side image 802 to be displayed according to the particular image, frame, set of information, or the like, corresponding to the side local frame value 832A. In an example, the side global frame value selection button 840A can include causing the obtained side image 802 and the obtained front image 804 to be displayed according to the particular images, frames, sets of information, or the like, corresponding to the global frame value 834.

While the examples above and below reference front and side views (e.g., two viewpoints), such techniques are applicable to other test configurations, such as including a single viewpoint, or more than two viewpoints.

Figure 9:
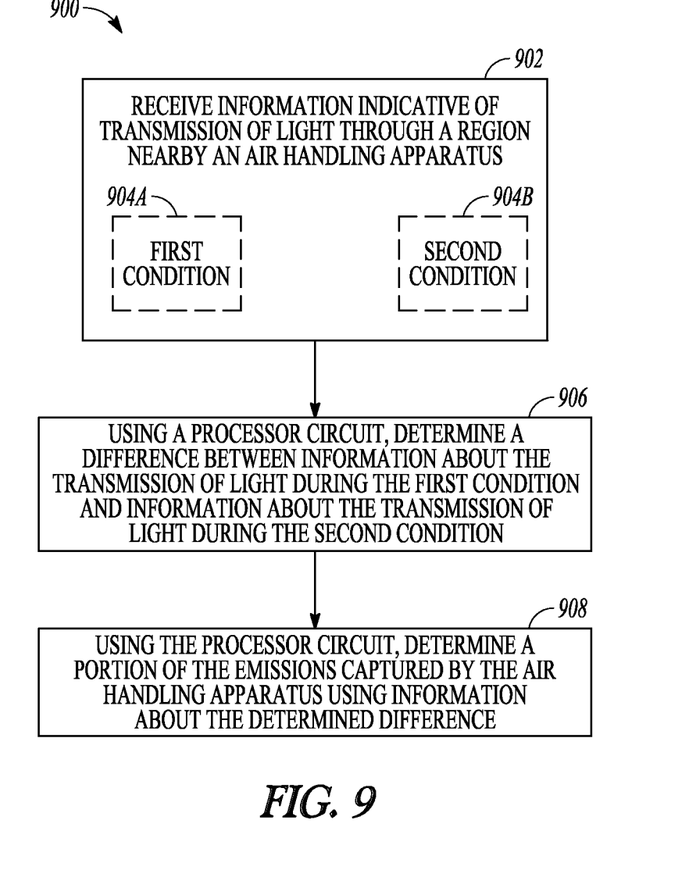
FIG. 9 illustrates generally a technique, such as a method, that can include determining a portion of the emissions captured by an air handling apparatus.

FIG. 9 illustrates generally a technique, such as a method, that can include receiving information indicative of transmission of light through a region nearby an air handling apparatus 902, the information can optionally include information indicative of a first condition wherein emissions to be captured by the air handling apparatus are suppressed 904A and information indicative of a second condition wherein emissions to be captured by the air handling apparatus are present 904B, using a processor circuit, determining a difference between information about the transmission of light during the first condition and information about the transmission of the light during the second condition 906, determining a portion of the emissions captured by the air handling apparatus using information about the determined difference 908.

Figure 10:
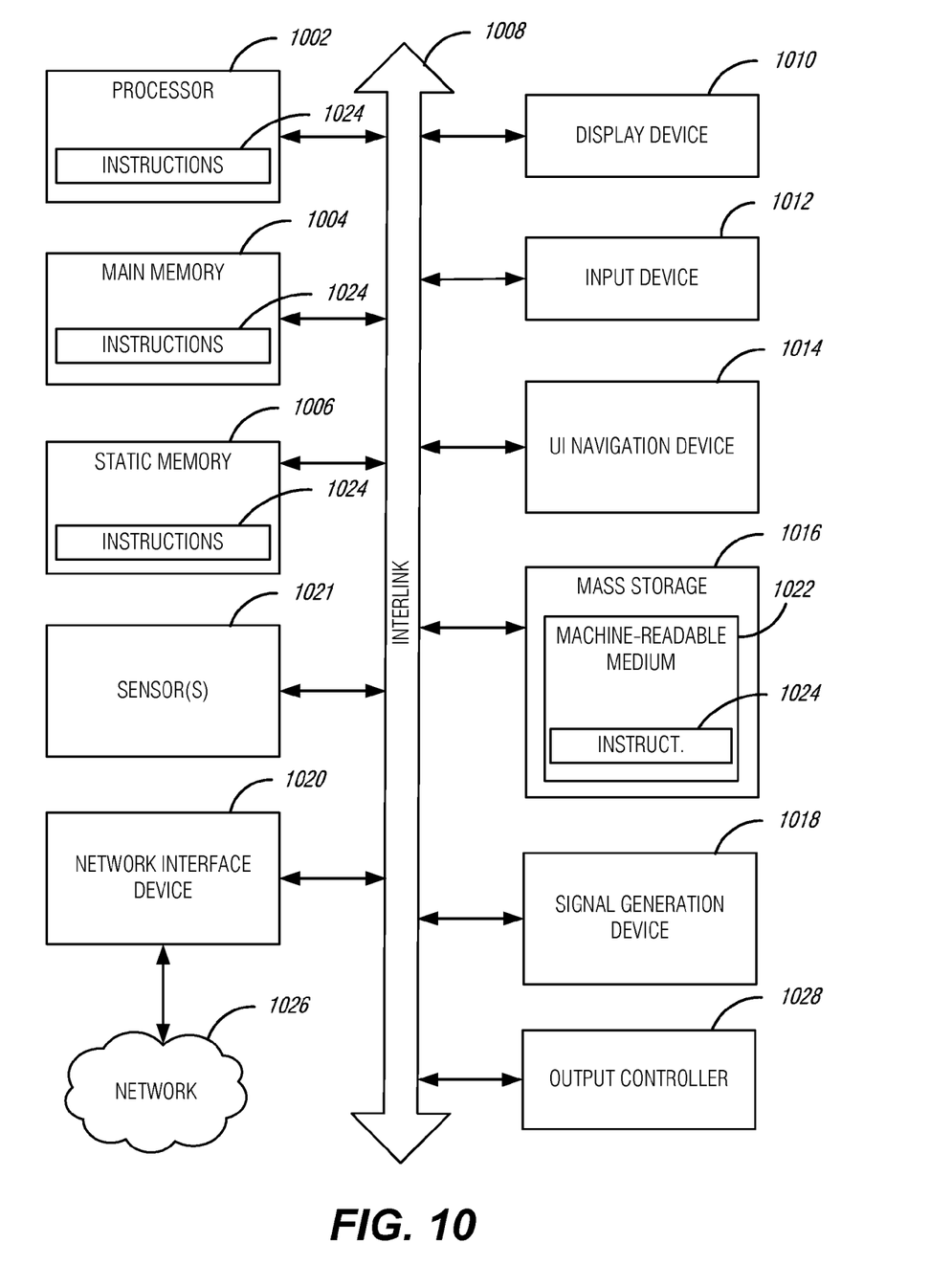
FIG. 10 illustrates generally an illustrative example of a block diagram of a machine upon which one or more embodiments can be implemented.

FIG. 10 illustrates a block diagram of an example machine 1000 upon which any one or more of the techniques (e.g., methodologies) discussed herein can perform. In alternative embodiments, the machine 1000 can operate as a standalone device or can be connected (e.g., networked) to other machines. In a networked deployment, the machine 1000 can operate in the capacity of a server machine, a client machine, or both in server-client network environments. In an example, the machine 1000 can act as a peer machine in peer-to-peer (P2P) (or other distributed) network environment. The machine 1000 can be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Examples, as described herein, can include, or can operate on, logic or a number of components, modules, or mechanisms. Modules are tangible entities (e.g., hardware) capable of performing specified operations when operating. A module includes hardware. In an example, the hardware can be specifically configured to carry out a specific operation (e.g., hardwired). In an example, the hardware can include configurable execution units (e.g., transistors, circuits, etc.) and a computer readable medium containing instructions, where the instructions configure the execution units to carry out a specific operation when in operation. The configuring can occur under the direction of the executions units or a loading mechanism. Accordingly, the execution units are communicatively coupled to the computer readable medium when the device is operating. In this example, the execution units can be a member of more than one module. For example, under operation, the execution units can be configured by a first set of instructions to implement a first module at one point in time and reconfigured by a second set of instructions to implement a second module.

Machine (e.g., computer system) 1000 can include a hardware processor 1002 (e.g., a central processing unit (CPU), a graphics processing unit (GPU), a hardware processor core, or any combination thereof), a main memory 1004 and a static memory 1006, some or all of which can communicate with each other via an interlink (e.g., bus) 1008. The machine 1000 can further include a display unit 1010, an alphanumeric input device 1012 (e.g., a keyboard), and a user interface (UI) navigation device 1014 (e.g., a mouse). In an example, the display unit 1010, alphanumeric input device 1012 and UI navigation device 1014 can be a touch screen display. The machine 1000 can additionally include a storage device (e.g., drive unit) 1016, a signal generation device 1018 (e.g., a speaker), a network interface device 1020, and one or more sensors 1021, such as a global positioning system (GPS) sensor, compass, accelerometer, or other sensor. The machine 1000 can include an output controller 1028, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

The storage device 1016 can include a machine readable medium 1022 that is non-transitory on which is stored one or more sets of data structures or instructions 1024 (e.g., software) embodying or utilized by any one or more of the techniques or functions described herein. The instructions 1024 can also reside, completely or at least partially, within the main memory 1004, within static memory 1006, or within the hardware processor 1002 during execution thereof by the machine 1000. In an example, one or any combination of the hardware processor 1002, the main memory 1004, the static memory 1006, or the storage device 1016 can constitute machine readable media.

While the machine readable medium 1022 is illustrated as a single medium, the term "machine readable medium" can include a single medium or multiple media (e.g., a centralized or distributed database, and/or associated caches and servers) configured to store the one or more instructions 1024.

The term "machine readable medium" can include any medium that is capable of storing, encoding, or carrying instructions for execution by the machine 1000 and that cause the machine 1000 to perform any one or more of the techniques of the present disclosure, or that is capable of storing, encoding or carrying data structures used by or associated with such instructions. Non-limiting machine readable medium examples can include solid-state memories, and optical and magnetic media. In an example, a massed machine readable medium comprises a machine readable medium with a plurality of particles having invariant (e.g., rest) mass. Accordingly, massed machine-readable media are not transitory propagating signals. Specific examples of massed machine readable media can include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 1024 can further be transmitted or received over a communications network 1026 using a transmission medium via the network interface device 1020 utilizing any one of a number of transfer protocols (e.g., frame relay, internet protocol (IP), transmission control protocol (TCP), user datagram protocol (UDP), hypertext transfer protocol (HTTP), etc.). Example communication networks can include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as Wi-Fi®, IEEE 802.16 family of standards known as WiMax®), IEEE 802.15.4 family of standards, peer-to-peer (P2P) networks, among others. In an example, the network interface device 1020 can include one or more physical jacks (e.g., Ethernet, coaxial, or phone jacks) or one or more antennas to connect to the communications network 1026. In an example, the network interface device 1020 can include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 1000, and includes digital or analog communications signals or other intangible medium to facilitate communication of such software.

Various Notes & Examples

Example 1 is a method of determining emissions captured, the method comprising receiving information indicative of transmission of light through a region nearby an air handling apparatus the information including information indicative of a first condition wherein emissions to be captured by the air handling apparatus are suppressed; and information indicative of a second condition wherein the emissions to be captured by the air handling apparatus are present; using a processor circuit, determining a difference between information about the transmission of light during the first condition and information about the transmission of light during the second condition; and using the processor circuit, determining a portion of the emissions captured by the air handling apparatus using information about the determined difference.

In example 2, the subject matter of example 1 can optionally include: wherein the receiving the information comprises receiving an image or a series of images of a surface illuminated by the light after propagating through the region nearby the air handling apparatus including receiving information indicative of a shadow cast on the surface due at least in part to variation in transmission of the light through the region.

In example 3, the subject matter of example 1 can optionally include: wherein the receiving the information comprises receiving information indicative of both spatial and temporal variation in the transmission of light through the region of interest.

In example 4, the subject matter of example 1 can optionally include: wherein the information indicative of the variation in transmission of light comprises digital imaging information.

In example 5, the subject matter of example 4 can optionally include: obtaining a first image or a first series of images using a digital camera to provide the information indicative of the first condition; and obtaining a second image or a second series of images using the digital camera to provide the information indicative of the first condition.

In example 6, the subject matter of example 4 can optionally include: wherein the digital imaging information is provided by a user, and wherein the method comprises receiving an indication of a portion of the digital imaging information corresponding to the first condition from the user and receiving an indication of a portion of the digital imaging information corresponding to the second condition from the user.

In example 7, the subject matter of example 1 can optionally include: wherein the receiving the information indicative of the variation in transmission of light through the region nearby the air handling apparatus includes receiving digital imaging corresponding to at least two viewing angles.

In example 8, the subject matter of example 7 can optionally include: wherein the at least two viewing angles include a pair of viewing angles that are substantially orthogonal to each other.

In example 9, the subject matter of example 1 can optionally include: wherein the determining the difference includes: identifying baseline intensity values on a location-by-location basis using a bitmap representation of the first condition; identifying intensity values on a location-by-location basis using a bitmap representation of the second condition; and determining a difference between a respective intensity value for a specified location corresponding to the second condition and a corresponding baseline intensity value for the specified location corresponding to the first condition.

In example 10, the subject matter of example 9 can optionally include: wherein the identifying baseline intensity values using the bitmap representations of the first and second conditions includes identifying pixel intensity values; and wherein the determining the difference between the respective intensity value for the specified location includes determining a difference between a pixel value for the specified location corresponding to the second condition, and a baseline pixel value for the specified location corresponding to the first condition.

In example 11, the subject matter of example 9 can optionally include: for a specified locus of locations, comparing respective magnitudes of the determined differences between the first and second conditions to a threshold; and classifying a location as a member of an effluent plume set of locations when the difference exceeds the threshold as indicated by the comparison.

In example 12, the subject matter of example 11 can optionally include: presenting a graphical representation of the specified locus of locations to a user including identifying the effluent plume.

In example 13, the subject matter of example 12 can optionally include: highlighting the effluent plume on the graphical representation using one or more of a specified intensity or color.

In example 14, the subject matter of example 11 can optionally include: identifying one or more of a spatial or temporal central tendency of information about the effluent plume set of locations.

In example 15, the subject matter of example 14 can optionally include: a user interface wherein the one or more of a spatial or temporal central tendency of information can be displayed.

In example 16, the subject matter of example 11 can optionally include: obtaining an indication of the specified locus of locations from a user.

In example 17, the subject matter of example 11 can optionally include: obtaining an indication of a dimensional reference datum from the user.

In example 18, the subject matter of example 11 can optionally include: determining an indication of a dimensional reference datum.

In example 19, the subject matter of example 11 can optionally include: determining a portion of the emissions captured includes determining respective differences between intensity values corresponding to the first and second conditions for locations outside the specified locus of locations; identifying particular locations as members of the effluent plume set at locations outside the specified locus of locations; and determining a relative indication of information about a proportion of the members of the effluent plume set outside the specified locus of locations as compared to members of the effluent plume set within the specified locus of locations.

In example 20, the subject matter of example 9 can optionally include: ignoring intensity values for locations having an intensity value below a specified absolute threshold.

In example 21, the subject matter of example 20 can optionally include: ignoring intensity values for a locus of locations within a specified distance of the locations having an intensity value below the specified absolute threshold.

In example 22, the subject matter of example 21 can optionally include: receiving an indication from a user of one or more of the specified absolute threshold or the specified distance.

In example 23, the subject matter of example 21 can optionally include: determining an indication of one or more of the specified absolute threshold or the specified distance.

Example 24 is a method of determining emissions captured, the method comprising: obtaining, by at least one camera, a first image or series of images of a surface on which light creates a shadow, the shadow indicative of transmission of the light through a region corresponding to a first condition wherein emissions to be captured by an air handling apparatus are suppressed; obtaining, by at least one camera, a second image or series of images of a surface on which light creates a shadow, the shadow indicative of transmission of the light through a region corresponding to a second condition wherein emissions to be captured by an air handling apparatus are present; identifying baseline pixel values using the first image or series of images; identifying pixel values using the second image or series of images; determining pixel intensity values wherein the pixel intensity values include differences between pixel values for specified locations corresponding to the second image or series of images and corresponding baseline pixel values for the specified locations corresponding to the first image or series of images; and using a processor circuit, determining a proportion of the emissions captured by the air handling apparatus using the first image or series of images, the second image or series of images, and the pixel intensity values.

Example 25 is a machine readable medium that is non-transitory, the machine readable medium including instructions that, when executed by a machine, cause the machine to perform operations comprising: receiving information indicative of transmission of light through a region nearby an air handling apparatus the information including: information indicative of a first condition wherein emissions to be captured by the air handling apparatus are suppressed; and information indicative of a second condition wherein the emissions to be captured by the air handling apparatus are present; and determining a difference between information about the transmission of light during the first condition and information about the transmission of light during the second condition; and determining a portion of the emissions captured by the air handling apparatus using information about the determined difference.

In example 26, the subject matter of example 25 can optionally include: wherein the information indicative of the variation in transmission of light comprises digital imaging information.

In example 27, the subject matter of example 25 can optionally include: wherein the receiving the information indicative of the variation in transmission of light through the region nearby the air handling apparatus includes receiving digital imaging corresponding to at least two viewing angles.

In example 28, the subject matter of example 25 can optionally include: wherein the determining the difference includes: identifying baseline intensity values on a location-by-location basis using a bitmap representation of the first condition; identifying intensity values on a location-by-location basis using a bitmap representation of the second condition; and determining a difference between a respective intensity value for a specified location corresponding to the second condition and a corresponding baseline intensity value for the specified location corresponding to the first condition.

In example 29, the subject matter of example 28 can optionally include: for a specified locus of locations, comparing respective magnitudes of the determined differences between the first and second conditions to a threshold; and classifying a location as a member of an effluent plume set of locations when the difference exceeds the threshold as indicated by the comparison.

In example 30, the subject matter of example 29 can optionally include: presenting a graphical representation of the specified locus of locations to a user including identifying the effluent plume.

In example 31, the subject matter of example 1 can optionally include: wherein the emissions comprise cooking effluent.

In example 32, the subject matter of example 1 can optionally include: wherein the air handling apparatus includes a vent hood.

In example 33, the subject matter of example 32 can optionally include: wherein the vent hood is wall or ceiling-mounted.

In example 34, the subject matter of example 1 can optionally include: wherein the air handling apparatus includes a down-draft ventilator.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code can form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) can be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features can be grouped together to streamline the disclosure. This should not be interpreted as intending that an unclaimed disclosed feature is essential to any claim. Rather, inventive subject matter can lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A method of determining emissions captured, the method comprising:
   receiving information indicative of transmission of light through a region nearby an air handling apparatus the information including:
      information indicative of a first condition wherein emissions to be captured by the air handling apparatus are suppressed; and
      information indicative of a second condition wherein the emissions to be captured by the air handling apparatus are present;
   using a processor circuit, determining a difference between information about the transmission of light during the first condition and information about the transmission of light during the second condition; and
   using the processor circuit, determining a portion of the emissions captured by the air handling apparatus using information about the determined difference.

2. The method of claim 1, wherein the receiving the information comprises receiving an image or a series of images of a surface illuminated by the light after propagating through the region nearby the air handling apparatus including receiving information indicative of a shadow cast on the surface due at least in part to variation in transmission of the light through the region.

3. The method of claim 1, wherein the receiving the information comprises receiving information indicative of both spatial and temporal variation in the transmission of light through the region of interest.

4. The method of claim 1, wherein the information indicative of the variation in transmission of light comprises digital imaging information.

5. The method of claim 4, comprising obtaining a first image or a first series of images using a digital camera to provide the information indicative of the first condition; and
   obtaining a second image or a second series of images using the digital camera to provide the information indicative of the first condition.

6. The method of claim 4, wherein the digital imaging information is provided by a user, and
   wherein the method comprises receiving an indication of a portion of the digital imaging information corresponding to the first condition from the user and receiving an indication of a portion of the digital imaging information corresponding to the second condition from the user.

7. The method of claim 1, wherein the receiving the information indicative of the variation in transmission of light through the region nearby the air handling apparatus includes receiving digital imaging corresponding to at least two viewing angles.

8. The method of claim 7, wherein the at least two viewing angles include a pair of viewing angles that are substantially orthogonal to each other.

9. The method of claim 1, wherein the determining the difference includes:
   identifying baseline intensity values on a location-by-location basis using a bitmap representation of the first condition;
   identifying intensity values on a location-by-location basis using a bitmap representation of the second condition; and
   determining a difference between a respective intensity value for a specified location corresponding to the second condition and a corresponding baseline intensity value for the specified location corresponding to the first condition.

10. The method of claim 9, wherein the identifying baseline intensity values using the bitmap representations of the first and second conditions includes identifying pixel intensity values; and
    wherein the determining the difference between the respective intensity value for the specified location includes determining a difference between a pixel value for the specified location corresponding to the second condition, and a baseline pixel value for the specified location corresponding to the first condition.

11. The method of claim 9, comprising, for a specified locus of locations, comparing respective magnitudes of the determined differences between the first and second conditions to a threshold; and
    classifying a location as a member of an effluent plume set of locations when the difference exceeds the threshold as indicated by the comparison.

12. The method of claim 11, comprising presenting a graphical representation of the specified locus of locations to a user including identifying the effluent plume.

13. The method of claim 12, comprising highlighting the effluent plume on the graphical representation using one or more of a specified intensity or color.

14. The method of claim 11, comprising identifying one or more of a spatial or temporal central tendency of information about the effluent plume set of locations.

15. The method of claim 14, comprising a user interface wherein the one or more of a spatial or temporal central tendency of information can be displayed.

16. The method of claim 11, comprising obtaining an indication of the specified locus of locations from a user.

17. The method of claim 11, comprising obtaining an indication of a dimensional reference datum from the user.

18. The method of claim 11, comprising determining an indication of a dimensional reference datum.

19. The method of claim 11, wherein determining a portion of the emissions captured includes determining respective differences between intensity values corresponding to the first and second conditions for locations outside the specified locus of locations;
 identifying particular locations as members of the effluent plume set at locations outside the specified locus of locations; and
 determining a relative indication of information about a proportion of the members of the effluent plume set outside the specified locus of locations as compared to members of the effluent plume set within the specified locus of locations.

20. The method of claim 9, comprising ignoring intensity values for locations having an intensity value below a specified absolute threshold.

21. The method of claim 20, comprising ignoring intensity values for a locus of locations within a specified distance of the locations having an intensity value below the specified absolute threshold.

22. The method of claim 21, comprising receiving an indication from a user of one or more of the specified absolute threshold or the specified distance.

23. The method of claim 21, comprising determining an indication of one or more of the specified absolute threshold or the specified distance.

24. A method of determining emissions captured, the method comprising:
 obtaining, by at least one camera, a first image or series of images of a surface on which light creates a shadow, the shadow indicative of transmission of the light through a region corresponding to a first condition wherein emissions to be captured by an air handling apparatus are suppressed;
 obtaining, by at least one camera, a second image or series of images of a surface on which light creates a shadow, the shadow indicative of transmission of the light through a region corresponding to a second condition wherein emissions to be captured by an air handling apparatus are present;
 identifying baseline pixel values using the first image or series of images;
 identifying pixel values using the second image or series of images;
 determining pixel intensity values wherein the pixel intensity values include differences between pixel values for specified locations corresponding to the second image or series of images and corresponding baseline pixel values for the specified locations corresponding to the first image or series of images; and
 using a processor circuit, determining a proportion of the emissions captured by the air handling apparatus using the first image or series of images, the second image or series of images, and the pixel intensity values.

25. A machine readable medium that is non-transitory, the machine readable medium including instructions that, when executed by a machine, cause the machine to perform operations comprising:
 receiving information indicative of transmission of light through a region nearby an air handling apparatus the information including:
  information indicative of a first condition wherein emissions to be captured by the air handling apparatus are suppressed; and
  information indicative of a second condition wherein the emissions to be captured by the air handling apparatus are present; and
 determining a difference between information about the transmission of light during the first condition and information about the transmission of light during the second condition; and
 determining a portion of the emissions captured by the air handling apparatus using information about the determined difference.

26. The machine readable medium of claim 25, wherein the information indicative of the variation in transmission of light comprises digital imaging information.

27. The machine readable medium of claim 25, wherein the receiving the information indicative of the variation in transmission of light through the region nearby the air handling apparatus includes receiving digital imaging corresponding to at least two viewing angles.

28. The machine readable medium of claim 25, wherein the determining the difference includes:
 identifying baseline intensity values on a location-by-location basis using a bitmap representation of the first condition;
 identifying intensity values on a location-by-location basis using a bitmap representation of the second condition; and
 determining a difference between a respective intensity value for a specified location corresponding to the second condition and a corresponding baseline intensity value for the specified location corresponding to the first condition.

29. The machine readable medium of claim 28, comprising, for a specified locus of locations, comparing respective magnitudes of the determined differences between the first and second conditions to a threshold; and
 classifying a location as a member of an effluent plume set of locations when the difference exceeds the threshold as indicated by the comparison.

30. The machine readable medium of claim 29, comprising presenting a graphical representation of the specified locus of locations to a user including identifying the effluent plume.

* * * * *